(12) United States Patent
Grossi et al.

(10) Patent No.: US 6,210,536 B1
(45) Date of Patent: Apr. 3, 2001

(54) POLYMERIZATION INHIBITORS FOR ACRYLIC ACIDS AND ESTERS

(75) Inventors: Anthony Vincent Grossi, Torrington; Paul Edwin Stott, Sandy Hook, both of CT (US)

(73) Assignee: Uniroyal Chemical Company, Inc., Middlebury, CT (US)

( * ) Notice: Subject to any disclaimer, the term of this patent is extended or adjusted under 35 U.S.C. 154(b) by 0 days.

(21) Appl. No.: 08/115,388

(22) Filed: Sep. 2, 1993

Related U.S. Application Data

(63) Continuation of application No. 07/729,515, filed on Jul. 12, 1991, now abandoned.

(51) Int. Cl.$^7$ ................ B00L 3/00; B00L 3/34; C07B 63/00
(52) U.S. Cl. ............ 203/8; 203/9; 203/DIG. 3; 203/DIG. 10; 203/DIG. 21; 544/37; 544/38; 564/112; 564/113
(58) Field of Search .................. 564/112, 113; 203/8, 9, DIG. 3, DIG. 10, DIG. 21; 544/37, 38

(56) References Cited

U.S. PATENT DOCUMENTS

| | | | |
|---|---|---|---|
| 2,901,459 | * 8/1959 | Merrifield | 564/112 |
| 2,938,922 | * 5/1960 | Tung | 564/112 |
| 3,751,378 | * 8/1973 | Copperthwaite et al. | 525/479 |

FOREIGN PATENT DOCUMENTS

| | | | |
|---|---|---|---|
| 975708 | * 10/1975 | (CA) | 203/8 |
| 49-124001 | * 11/1974 | (JP) . | |

OTHER PUBLICATIONS

Tung et al., Chem. Abs. 53:1807h–1808a (1959).*
Hand et al., Chem. Abs. 51:15990c–e (1957).*
Zolotarevskaya et al., Chem. Abs. 70:20820r (1969).*
Marumo et al., Chem. Abs. 106:137951n (1987).*

\* cited by examiner

Primary Examiner—Peter O'Sullivan
(74) Attorney, Agent, or Firm—Daniel Reitenbach

(57) ABSTRACT

This invention is directed to certain N,N'-dinitroso phenylenediamines useful as polymerization inhibitors for acrylic acids and esters thereof. Also disclosed are compositions containing such compounds, and methods for inhibiting polymerization using such compounds and compositions.

9 Claims, No Drawings

POLYMERIZATION INHIBITORS FOR ACRYLIC ACIDS AND ESTERS

This is a continuation of application Ser. No. 729,515, filed Jul. 12, 1991, now abandoned.

BACKGROUND OF THE INVENTION

1. Field of the Invention

This invention relates to compounds and compositions useful as polymerization inhibitors for acrylic acids and esters thereof. It also is concerned with a method for inhibiting polymerization of acrylic acids and esters thereof, particularly on a manufacturing scale, by use of these compounds and compositions.

Acrylic acid, methacrylic acid, and esters thereof have wide application as raw materials for fibers and plastics. Since these compounds have reactive unsaturated bonds in their molecules they are prone to polymerize under the conditions encountered during purification, manufacturing or storage. Commercial processes for the manufacture of acrylic and methacrylic acids and esters typically produce products contaminated with various impuruties. These impurities must be removed in order for the monomer product to be suitable for most applications. Such purification is generally accomplished by distillation.

Polymerization is likely to occur during distillation and may occur as a result of the presence of heat, light, oxygen and other conditions. It is therefore most desirable to minimize or eliminate the tendency of acrylic acids or acrylates to polymerize during manufacturing, thus assuring that the vessels and pipes used to transport the material during production remain clean and the reactors free of build up of high viscosity, high molecular weight, polymerized material.

2. Description of Related Art

Japanese patent application 48-35699 is directed to the stabilization of styrene, chloroprene, butadiene, isoprene, or acrylic acid derivatives with various compounds including certain N,N'-dinitroso compounds.

Japanese patent application 48-38399 is directed to stabilization of acrylates or methacrylates with certain N-nitrosoamine compounds.

U.S. Pat. No. 3,816,267 is directed to inhibition of acrylate polymerization during distillation by the use of a quinone and an enol derivative of a quinone. U.S. Pat. No. 4,338,162 is directed to the inhibition of vinyl polymerization of a 2-isocyanatoalkyl ester of unsaturated carboxylic acid with certain nitrogen oxides. U.S. Pat. No. 3,959,358 is directed to polymerization inhibition of acrylate esters by use of an alkyl-substituted phenolic compound.

During distillation of acrylic acids and esters high distillation temperatures are required to achieve a throughput which is efficient and economical. These high temperatures, however, also result in an increased rate of polymerization leading to unacceptable levels of polymer in the distillation apparatus. Accordingly, there exists a strong need for a polymerization inhibitor which will protect the acrylic system from polymerization during distillation at high temperatures.

SUMMARY OF THE INVENTION

This invention is directed to N,N'-dinitroso phenylenediamine compounds useful as polymerization inhibitors, which have the following structure (I):

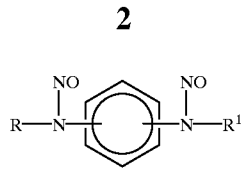

wherein R is $C_1$–$C_{12}$ alkyl or $C_6$–$C_{10}$ aryl; R1 is $C_1$–$C_{12}$ alkyl, $C_6$–$C_{10}$ aryl, $C_7$–$C_{11}$ aralkyl, and $C_7$–$C_{16}$ alkaryl.

This invention is also directed to polymerization inhibitor compositions comprising:
(a) at least one compound having structure (I) as defined above;
(b) a phenothiazine having the structure

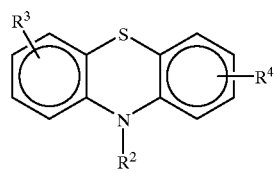

wherein R2 is hydrogen or $C_1$–$C_{12}$ alkyl; and R3 and R4 are each independently selected from the group consisting of hydrogen, $C_6$–$C_{10}$ aryl, $C_7$–$C_{11}$ aralkyl, $C_7$–$C_{16}$ alkaryl and $C_1$–$C_{12}$ alkyl; and, optionally
(c) hydroquinone or hydroquinone momomethyl ether, and optionally
(d) a phenylenediamine compound having the following structure

wherein $R^6$ is $C_1$–$C_{12}$ alkyl, $C_6$–$C_{10}$ aryl or $C_7$–$C_{16}$ alkaryl; and $R^7$, $R^8$ and $R^9$ are independently selected from the group consisting of hydrogen, $C_1$–$C_{12}$ alkyl, $C_3$–$C_{12}$ cycloalkyl, $C_7$–$C_{11}$ aralkyl and $C_7$–$C_{16}$ alkaryl. The above components will be hereinafter be referred to as composition I.

In another aspect, this invention is directed to an acrylic or methacrylic acid or ester composition stabilized against polymerization by an effective amount of a compound having structure I or by an effective amount of composition I.

In yet another aspect, this invention is directed to a method for inhibiting polymerization of an acrylic or methacrylic acid or ester composition, said method comprising adding an effective amount of the polymerization inhibitor of structure I or composition I.

DETAILED DESCRIPTION OF THE INVENTION

The subject N,N'-dinitroso phenylenediamine derivatives may be prepared from phenylenediamine, sodium nitrite, and a suitable mineral acid (such as sulfuric or hydrochloric), as more fully set forth below in Examples 1–3.

Preferred N,N'-dinitroso phenylenediamine compounds include those wherein the amine groups are in the para position. Particularly preferred are compounds wherein R is $C_3$–$C_7$ alkyl and $R^1$ is phenyl or $C_3$–$C_7$ alkyl.

Illustrative preferred N,N'-dinitroso phenylenediamine compounds which may be employed include N-phenyl-N'- isopropyl dinitroso-p-phenylenediame, N-phenyl-N'-(1,3-dimethylbutyl)dinitroso-p-phenylenediamine, N-phenyl-N'-(1,4-dimethylpentyl)-dinitroso-p-phenylenediamine, and N,N'-bis(1,4-dimethylpentyl)-dinitroso-p-phenylenedimine. Moreover, mixtures of N,N'-dinitroso phenylenediamines may be employed.

The phenothiazine compounds are generally known, and their synthesis would be readily apparent to one skilled in the art. Particularly suitable phenothiazine compounds which may be employed in the compositions of the present invention include phenothiazine, 2-methylphenothiazine, 2-octylphenothiazine, 2-nonylphenothiazine, 2,8-dimethylphenothiazine, 3,7-dimethylphenothiazine, 3,7-diethylphenothiazine, 3,7-dibutylphenothiazine, 3,7-dioctylphenothiazine, 2,8-dioctylphenothiazine, 3,7-dinonylphenothiazine, 2,8-dinonylphenothiazine, 2(alpha, alpha-dimethylbenzyl)phenothiazine, 3,7-bis-(alpha,alpha-dimethylbenzyl)phenothiazine, 2,8-bis-(alpha, alpha-dimethylbenzyl)phenothiazine. Moreover, mixtures of two or more phenothiazine and N,N'-dinitroso phenylenediamine comounds may also be employed.

The hydroquinone or hydroquinone monomethyl ether are compounds which are known as antioxidants and, specifically, as monomer stabilizers. They have been used as shelf stabilizers for acrylic monomers.

The phenylenediamine compounds (optional component (d)) are also generally known, and their synthesis would be readily apparent to one skilled in the art. Preferred phenylenediamine compounds include those wherein the amine groups are in the para position. Particularly preferred compounds are the para-phenylenediamines wherein $R^7$ and $R^8$ are hydrogen; $R^6$ is alkyl or phenyl; and $R^9$ is $C_3$–$C_8$ alkyl or $C_3$–$C_8$ cycloalkyl.

Illustrative of the preferred phenylenediamine compounds which may be employed include N,N'-bis(1,4-dimethylpentyl)-p-phenylenediamine, N-phenyl-N'-isopropyl-p-phenylenediamine, N-phenyl-N'-(1,3-dimethylbutyl)-p-phenylenediamine, N-phenyl-N'-(1,4-dimethylpentyl)-p-phenylenediamine and N-phenyl-N'-cyclohexyl-p-phenylenediamine. Moreover, mixtures of phenylenediamine compounds may also be employed. The phenylenediamine compounds may be of the oxygenated species as described in U.S. Pat. No. 4,774,374 to Abruscato et al.

The N,N'-dinitroso phenylenediamine and phenothiazine/hydroquinone compounds are generally employed in weight ratios of between 10:1 and 1:10. Preferably, weight ratios of between 4:1 and 1:4 are employed. Most preferred ratios include those from 3:1 and 1:3. If a phenylenediamine is employed, it is generally present in weight ratios of between 10:1 and 1:10, based on the weight of N,N'-dinitroso phenylenediamine.

The polymerization inhibitor compositions of this invention may further comprise a solvent such as toluene, MIBK (methyl isobutyl ketone), isobutyl acetate, isopropyl ether, acrylic acid, methacrylic acid, water, and the like.

A primary use of the polymerization inhibitor compounds and compositions of this invention is to prevent the polymerization of acrylic and methacrylic acid and esters thereof during their purification by distillation to remove unreacted starting materials and distillable by-products. Typically, this involves the sequential distillation of the acrylic or methacrylic acid or ester reaction product through a plurality of distillation columns. In the first of such columns, a relatively large amount of starting material and by-products will be present, while in the last column essentially pure acrylic acid or ester compound, plus polymerization inhibitors and heavy, nondistillable by-products, will be present.

The method of this invention involves adding to an acrylic or methacrylic acid or ester an effective amount of the polymerization inhibitor compound or composition described herein. When the polymerization inhibitor composition of this invention is employed with a hydroquinone compound and/or a phenylenediamine during the purification or distillation of the acrylic acid or ester, it is preferred that oxygen, whether in the form of air (either added or ambient) or otherwise, be present. It is noted that the polymerization inhibitor compounds and compositions of this invention will be effective for uses other than distillation, for example during shipment or storage of the acrylic compound.

The method of this invention entails the addition of an effective amount of a polymerization inhibitor compound or composition to acrylic or methacrylic acid or esters thereof. Although the amount of polymerization inhibitor required will vary somewhat, based on such factors as the particular N,N'-dinitroso phenylenediamine and the phenothiazine/hydroquinone species employed, such an effective amount may be readily determined by experimentation. Generally, such an effective amount will be between about 50 and 5,000 parts per million by weight of acrylic/methacrylic compound.

The polymerization inhibitor compounds and compositions of this invention will provide stability against polymerization at temperatures typically employed for purification of acrylic acids amd esters, from about 90° to about 140° C., for time periods in excess of those typically employed for such purifications.

In actual production of acrylic and methacrylic acids and esters, it is desired by the manufacturers that the plants run for 24 hours/7 days per week; that is, with as little downtime as possible, preferably none. The current state of the art requires shut-down as often as every 90 days to clean the residue of the unwanted polymer in the distillation apparatus.

EXAMPLES

The following examples are intended to further illustrate the present invention and are not intended to limit the scope of the invention in any manner whatsoever.

Example 1

Preparation of N-phenyl-N'-isopropyl dinitroso-p-phenylenediamine (Compound No. 1)

To a one-liter round bottom flask is added 109 grams of hexanol and 90.4 g (0.40 moles) of N-phenyl-N'-isopropyl p-phenylenediamine. A solution containing 61.2 g of sodium nitrite (0.88 moles) in 122.4 g of water (a 33% solution) is added to the hexanol solution all at once. A solution containing 40 g of concentrated sulfuric acid in 80 g of water (a 33% solution) is added dropwise over a 30 minute period keeping the temperature below 30° C. Stirring is continued for another 30 minutes. The precipitate is collected by filtration and washed well with water yielding 100 g (88%) of N-phenyl-N'-isopropyl dinitroso-p-phenylenediamine. Recrystallization from aqueous methanol gave a melting point of 85–89° C.

Example 2

Preparation of N,N'-bis(1,4-dimethylpentyl)-dinitroso-p-phenylenediamine (Compound No. 2)

A process essentially identical to that described in Example 1 above was carried out, except N,N'-bis(1,4- dimethylpentyl)-p-phenylenediamine was used as a starting material in place of N-phenyl N'-isopropyl p-phenylenediamine. After stirring for the previously specified 30 minutes, the layers were separated, and hexanol was stripped from the organic phase leaving a brown liquid, 128 g, 88.4%. To clean the product, it was dissolved in toluene and extracted twice with water. The toluene layer was then stripped leaving N,N'-bis(1,4-dimethylpentyl)dinitroso-p-phenylenediamine, a brown liquid. The structure was confirmed by infrared spectroscopy.

Example 3

Preparation of N-phenyl-N'(1,4-dimethylpentyl)-dinitroso p-phenylenediamine and N-phenyl-N'(1,3-dimethylbutyl)-dinitroso-p-phenylenediamine 60/40 blend (Compound No. 3)

The procedure detailed in Example 1 was followed, except a 60/40 blend of N-phenyl-N'-(1,4-dimethylpentyl) p-phenylenediamine and N-phenyl-N'-(1,3-dimethylbutyl) p-phenylenediamine was used. The stirring time was lengthened to two hours. The solid was collected by filtration and washed well with water. Recrystallization from methanol yielded a solid with a melting point of 51–56° C.

Example 4

Onset of Polymerization Screening Test Procedure

The following test is an initial screening procedure which is a timed test to determine how long it takes for polymerization to occur, which is a measure of inhibitor efficiency. For this test, shelf inhibitor is removed from acrylic acid by distillation. A 0.1% stock solution of each inhibitor in acrylic acid is prepared. Solutions containing 10 ppm inhibitor are prepared from the stock solutions and put in a test tube.

Each test tube, equipped with an internal oil tube and thermocouple, is placed in a constant temperature oil bath at 80° C. The first sign of an exotherm, read from a chart recorder, is the "onset of polymerization" time, expressed in hours. The longer the time until onset of polymerization, the better the performance of the inhibitor candidate. The tests for each compound were run twice to increase the reliability of the results. The results are set forth in Table I.

TABLE I

Testing Results/Onset of Polymerization Test

| Inhibitor | Time (hrs) |
| --- | --- |
| Blank | 7.65 |
| Blank | 5.8 |
| PTZ/HQ[1] | 142.95 |
| PTZ/HQ | 165 |
| Compound 1 | 6.0 |
| Compound 1 | 5.95 |
| Compound 2 | 3.0 |
| Compound 2 | 4.2 |
| Hydroquinone | 0.65 |
| Hydroquinone | 5.3 |

In Examples 5–7 below, the compounds and compositions of this invention are shown to be polymerization inhibitors in various distillation procedures. Unless otherwise noted, the distillation screening apparatus used in these examples consists of a distillation pot fitted with a tray distillation column, pot thermometer, graduated addition funnel, inhibitor addition funnel, magnetic stirrer, and a bottom vacuum take-off.

The distillation column was fitted with a distillation head consisting of a thermometer, cold finger, vacuum take-off, inhibitor addition funnel, and valved condensate vacuum take-off.

Example 5

Initial Screening Distillation Test

To 500 grams of acrylic acid are added 0.2% phenothiazine and 0.2% hydroquinone. The solution is placed in the distillation pot. 300 ml of commercial acrylic acid is placed in the addition funnel.

The contents of the pot is distilled at 105° C. under reduced pressure. The distillation is run at a 1:4 reflux rate. Acrylic acid is removed from the overhead at a rate of 1 ml/min and the addition of acrylic acid to the distillation pot is also 1 ml/min to maintain a constant pot volume.

Acrylic acid containing 20,000 ppm of phenothiazine and 20,000 ppm of hydroquinone is added to the system at a rate of 10 ml/hr directly to the cold finger in the overhead to protect the column from polymerization.

The tested inhibitor is added directly to the acrylic acid in the distillation pot at a rate of 10 ml/hr. Air is added to the distillation pot at a rate of approximately 8 ml/min. The distillation is run for 5 hours. The columns, pot, dead space, and overhead were inspected hourly for the formation of any polymer.

The following data in Table II show the results of several inhibitors, and known compounds as controls.

TABLE II

| Inhibitors | Solvent | Dinitroso Inhibitor (ppm/hour) | Polymer Formation in system |
| --- | --- | --- | --- |
| PTZ/HQ[1] | none | n/a | yes[2] |
| PTZ/HQ + Compound 1 | toluene | 50 | no |
| PTZ/HQ + Compound 2 | acrylic acid | 50 | no |
| PTZ/HQ + NBDA[3] | acrylic acid | 100 | no |

Notes for Table II:
[1]PTZ/HQ = a 50:50 blend of phenothiazine:hydroquinone
[2]Polymer formed within the first 30 minutes
[3]NBDA = 50% N,N'-bis(1,4-dimethylpentyl)-p-phenylenediamine and 50% Compound 2

Example 6

Measured Polymerization Test

To 500 g of freshly distilled acrylic acid is added 100 ppm phenothiazine and the solution is placed in the distillation pot. 300 ml of freshly distilled acrylic acid containing 100 ppm of phenothiazine is placed in the addition funnel.

The contents of the pot is distilled at 105° C. under 185 mm Hg. The distillation is run at a 1:4 reflux rate. Acrylic acid is removed from the overhead at a rate of 12 ml/hr and removed from the bottoms at a rate of 48 ml/hr. Acrylic acid is added to the distillation pot at a rate of 60 ml/hr to maintain a constant pot volume.

Freshly distilled acrylic acid containing 500 ppm of phenothiazine is added to the system at a rate of 10 ml/hr directly to the cold finger in the overhead to protect the column from polymerization. The inhibitor is added directly to the acrylic acid in the distillation pot at a rate of 10 ml/hr.

The distillation was run for 5 hours, after which time the columns, pot, dead space, and overhead was inspected hourly for the formation of polymer. Results of the Measured Polymerization Test for various inhibitors are summarized below in Table III.

TABLE III

Testing Results/Measured Polymerization Test

| Inhibitor(s) | Level of Inhibitor (ppm) | Total Polymer after 5 hrs. | |
|---|---|---|---|
| | | Run #1 | Run #2 (gms) |
| PTZ | 500 | 2.17 | 2.52 |
| PTZ/Cmpd #1 | 500/4600 | trace | 0.05 |
| PTZ/Cmpd #1 | 500/2300 | 0.88 | N/A |

Example 7

Seed Growth Test

A. Determination of Seed Activity 500 grams of acrylic acid are placed in the distillation pot. Approximately 0.04 grams of seed polymer (polyacrylic acid) is placed in a stainless steel basket with a lid and suspended in the overhead section to eliminate contact with liquid material. Sixty ml/hr of freshly distilled acrylic acid is added. The take/off rate is 60 ml/hr from the overhead, which is approximately a 1:4 ratio.

The distillation is carried out at 105° C. and 185 mm Hg for a test period of five hours. Phenothiazine and hydroquinone (2% each by weight in acrylic acid is added at the midpoint of the condenser for protection of the column from polymerization) at a rate of 10 ml/hr. 400 ppm of each of these substances are also added to the bottoms to eliminate polymer formation in the pot.

At the end of the test, the seed is washed well with methanol, dried to constant weight in a vacuum oven, and reweighed. Percent seed growth is calculated to determine if the polymer seed is active.

B. Determination of Inhibition

In this part, active seed determined in part A above is used. The part A procedure is repeated, except that 2500 ppm of either phenothiazine/hydroquinone, Compound 1 or Compound 2 in acrylic acid is added to the bottoms at 10 ml/hr. The results are set forth in Table IV.

TABLE IV

Testing Results/Seed Growth Test

| Only | Inhibitor Candidate Used | |
|---|---|---|
| PTZ/HQ | Compound 1 | Compound 2 |
| 541% | 17% | 15% |
| 934% | 8.5% | 72% |
| 361% | 14% | 64% |
| 2366% | — | 38% |
| 930% | — | — |
| 495% | — | — |

It will be clear from the preceding data in Examples 4–7 that the compositions of the present invention exhibit unexpected activity. For example, in the initial screening test of Example 4, the combination of phenothiazine and hydroquinone gave good results and was chosen as a candidate for the distillation tests of Examples 5–7, where it gave unacceptable performance. On the other hand, Compounds 1 and 2 gave unacceptable results in the Example 4 polymerization onset test, and thus would not normally be considered as viable inhibitor candidates in the distillation tests. However, when combined with phenothiazine and hydroquinone in the distillation test, which is closer to the actual use situations where polymerization inhibition in production and purification of acrylic compounds is needed, acceptable results are surprisingly obtained.

What is claimed is:

1. A method for inhibiting the polymerization of an acrylic or methacrylic acid or ester during distillation of the acrylic or methacrylic acid or ester, which comprises conducting the distillation in the presence of an effective amount of a polymerization inhibitor composition consisting essentially of:

(a) at least one N,N'-dinitroso phenylenediamine compound having the structure:

wherein R is $C_1$–$C_{12}$ alkyl or $C_6$–$C_{10}$ aryl; $R^1$ is $C_1$–$C_{12}$ alkyl, $C_6$–$C_{10}$ aryl, $C_7$–$C_{11}$ aralkyl, or $C_7$–$C_{16}$ alkaryl; and (b) at least one phenothiazine having the structure:

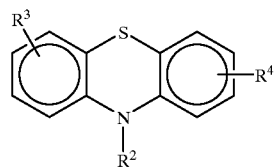

wherein $R^2$ is hydrogen or $C_1$–$C_{12}$ alkyl; and $R^3$ and $R^4$ are each independently selected from the group consisting of hydrogen, $C_6$–$C_{10}$ aryl, $C_7$–$C_{11}$ aralkyl, $C_7$–$C_{16}$ alkaryl and $C_1$–$C_{12}$ alkyl;

(c) optionally a hydroquinone or hydroquinone monomethyl ether; and (d) optionally a phenylenediamine compound having the following structure

wherein $R^6$ is $C_1$–$C_{12}$ alkyl, $C_6$–$C_{10}$ aryl or $C_7$–$C_{16}$ alkaryl; and $R^7$, $R^8$ and $R^9$ are independently selected from the group consisting of hydrogen, $C_1$–$C_{12}$ alkyl, $C_3$–$C_{12}$ cycloalkyl, $C_7$–$C_{11}$ aralkyl and $C_7$–$C_{16}$ alkaryl.

2. A method in accordance with claim 1 wherein in component (a), R and $R^1$ are $C_3$–$C_7$ alkyl.

3. A method in accordance with claim 1 wherein component (a) is selected from the group consisting of N-phenyl-N'-(1,3-dimethylbutyl)dinitroso-p-phenylene-diamine, N-phenyl-N'-(1,4-dimethylpentyl)-dinitroso-p-phenylenediamine, N,N'-bis(1,4-dimethylpentyl)dinitroso-p-phenylenedimine, and mixtures thereof.

4. A method in accordance with claim 1 wherein component (b) is selected from the group consisting of phenothiazine, 2-methylphenothiazine, 2-octylphenothiazine, 2-nonylphenothiazine, 2,8-dimethylphenothiazine, 3,7-dimethylphenothiazine, 3,7-diethylphenothiazine, 3,7-dibutylphenothiazine, 3,7-dioctylphenothiazine, 2,8-dioctylphenothiazine, 3,7-dinonylphenothiazine, 2,8-dinonylphenothiazine, 2(alpha, alpha-dimethylbenzyl)phenothiazine, 3,7-bis-(alpha,alpha-dimethylbenzyl)phenothiazine, 2,8-bis-(alpha, alpha-dimethylbenzyl)phenothiazine, and mixtures thereof.

5. A method in accordance with claim 1 wherein component (c) is hydroquinone.

6. A method in accordance with claim 1 wherein component (d) is selected from the group consisting of N,N'-bis(1,4-dimethylpentyl)-p-phenylenediamine, N-phenyl-N'-isopropyl-p-phenylenediamine, N-phenyl-N'-(1,3-dimethylbutyl)-p-phenylenediamine, N-phenyl-N'-(1,4-dimethylpentyl)-p-phenylenediamine, N-phenyl-N'-cyclohexyl-p-phenylenediamine, and mixtures thereof.

7. A method in accordance with claim 1 wherein the weight ratio of component (a) to components (b) and (c) combined, is between 10:1 and 1:10.

8. A method in accordance with claim 4 wherein the weight ratio is between 3:1 and 1:3.

9. A method in accordance with claim 1 wherein the weight ratio of component (a) to component (d) is between 10:1 and 1:10.

* * * * *